(12) United States Patent
Wu et al.

(10) Patent No.: US 7,391,844 B2
(45) Date of Patent: Jun. 24, 2008

(54) METHOD AND APPARATUS FOR CORRECTING FOR BEAM HARDENING IN CT IMAGES

(75) Inventors: Xiaoye Wu, Rexford, NY (US); Piero Ugo Simoni, Greenfield, WI (US); Thomas Louis Toth, Brookfield, WI (US); Neil Barry Bromberg, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 204 days.

(21) Appl. No.: 11/036,618

(22) Filed: Jan. 14, 2005

(65) Prior Publication Data

US 2006/0159223 A1 Jul. 20, 2006

(51) Int. Cl.
*A61B 6/00* (2006.01)

(52) U.S. Cl. .......................... 378/18; 378/207

(58) Field of Classification Search ............... 378/4–20, 378/156, 207, 901
See application file for complete search history.

(56) References Cited

U.S. PATENT DOCUMENTS

| 4,097,736 A * | 6/1978 | Jacobson et al. ............. 378/207 |
|---|---|---|
| 4,149,081 A * | 4/1979 | Seppi ............................... 378/5 |
| 4,873,707 A * | 10/1989 | Robertson ..................... 378/18 |
| 5,293,312 A * | 3/1994 | Waggener ..................... 378/14 |
| 5,335,260 A * | 8/1994 | Arnold ........................ 378/207 |
| 5,450,462 A | 9/1995 | Toth et al. ..................... 378/16 |
| 5,579,359 A | 11/1996 | Toth ............................. 378/19 |
| 5,949,842 A * | 9/1999 | Schafer et al. ................... 378/4 |
| 6,115,487 A | 9/2000 | Toth et al. ..................... 382/131 |
| 6,173,038 B1 * | 1/2001 | Siffert et al. ................... 378/56 |
| 6,266,434 B1 | 7/2001 | Toth et al. ..................... 382/131 |
| 6,325,539 B1 | 12/2001 | Bromberg et al. ............ 378/207 |
| 6,327,329 B1 | 12/2001 | Bromberg et al. ............. 378/19 |
| 6,430,252 B2 * | 8/2002 | Reinwand et al. ............... 378/8 |
| 6,438,197 B2 * | 8/2002 | Stierstorfer ..................... 378/8 |
| 6,904,120 B2 * | 6/2005 | Wu et al. ....................... 378/19 |
| 7,086,780 B2 * | 8/2006 | Wu et al. ..................... 378/207 |
| 2004/0264628 A1 * | 12/2004 | Besson ........................... 378/5 |
| 2005/0259784 A1 * | 11/2005 | Wu et al. ....................... 378/19 |
| 2006/0023844 A1 * | 2/2006 | Naidu et al. ................. 378/210 |

FOREIGN PATENT DOCUMENTS

| EP | 0981997 A1 | 3/2000 |
|---|---|---|
| EP | 1355321 A2 | 10/2003 |
| EP | 1389444 A1 | 2/2004 |

* cited by examiner

*Primary Examiner*—Courtney Thomas
*Assistant Examiner*—Alexander Taningco
(74) *Attorney, Agent, or Firm*—Armstrong Teasdale LLP (57) ABSTRACT

A method for determining a correction for beam hardening in CT images includes obtaining air scans at a plurality of kVp's, determining detection efficiencies for detector elements of the CT imaging apparatus, and estimating projection values through a combination of at least two different materials of different thicknesses. The method further includes determining a transfer function that translates the estimated projection values into ideal projection values for at least two of the different materials and storing the transfer function as the beam hardening correction for images of the CT imaging apparatus.

23 Claims, 3 Drawing Sheets

METHOD AND APPARATUS FOR CORRECTING FOR BEAM HARDENING IN CT IMAGES

BACKGROUND OF THE INVENTION

This invention relates generally to computed tomographic (CT) imaging systems, and more particularly to correction of artifacts resulting from beam hardening resulting from high-density materials.

It is known that in the absence of bones or other high-contrast materials, modern CT images produced from scans of patients are artifact-free, mainly due to accurate spectral calibration that removes artifacts for water or soft tissue. However, such images are usually not free of image artifacts resulting from high-density materials.

Image artifacts resulting from high-density materials can be divided into several categories according to their cause. These categories include (1) beam hardening, (2) beam hardening induced detector spectral response variation, and (3) aliasing and photon starvation. Configurations of the present invention are particularly suited for correcting artifacts in the first two categories. Various configurations of the present invention can be used in conjunction with other methods and/or apparatus that correct artifacts in the third category.

The polychromatic nature of x-ray sources used in CT imaging systems induces beam-hardening artifacts in the reconstructed images. In a human body being imaged, there are two main components that lead to distinct beam hardening behaviors: one arising from soft tissue and the other from bone. To complicate this matter, detection efficiency of detector elements changes with x-ray spectrum hardened by different materials, resulting in detection system related image artifacts. In practice, for modern CT scanners, a spectral calibration procedure is performed. This calibration is very effective for water or soft tissue. However, these calibration procedures do not correct for beam hardening problems resulting from other materials. In addition, relative variations in detector response between detector channels is commonly induced by high-density materials, and these calibration procedures are not effective in correcting for these induced variations. For example, head images often require an extra beam hardening correction to remove artifacts for the skull and the complex bone structures inside the head. It is known to correct bone induced beam hardening through a second-pass iteration, where projections due to bones are used to assess and to correct beam hardening in the images. However, the correction for bone induced beam hardening is not effective to correct detector spectral response variations, which tend to create banding or center artifacts in images. As a result, extremely strict requirements are often needed to the guarantee the similarity of detector spectral response behaviors, especially for the detector channels near the isocenter in a third generation CT system.

The purpose of spectral related calibrations in CT imaging systems is to generate a functional form or table that re-maps measured projection values (normalized and minus logged) to its corresponding x-ray path length. The x-ray path length in which the x-rays are hardened can vary, resulting in a variation in the effective attenuation coefficient. This re-mapping ensures that a fixed value attenuation coefficient is formed regardless of the variation in x-ray path length in which the x-rays are hardened. At the same time, detector-related variation is also removed. Known calibrations are performed with only one material, namely, water. Experimental calibration with a mixture of different materials is difficult to perform. Such calibration, were it feasible, would be complex and time consuming.

BRIEF DESCRIPTION OF THE INVENTION

Some aspects of the present invention therefore provide a method for determining a correction for beam hardening in CT images in a CT imaging apparatus. The method includes obtaining air scans at a plurality of kVp's, determining detection efficiencies for detector elements of the CT imaging apparatus, and estimating projection values through a combination of at least two different materials of different thicknesses. The method further includes determining a transfer function that translates the estimated projection values into ideal projection values for at least two of the different materials and storing the transfer function as the beam hardening correction for images of the CT imaging apparatus.

In other aspects, the present invention provides a method for determining a correction for beam hardening in computed tomographic (CT) images. The method includes determining projection data $P(a,b,i)$ for parameters a and b over a dynamic range, where a is a thickness of a first material A, b is a thickness of a second, different material B, i is a detector index, and $P(a,b,i)$ is a logarithmic function of a ratio of an expected signal through a thickness of first material A, b thickness of second, different material B at detector index i and an expected air measurement signal at detector index i. The method further includes determining projection data $P(0,b,i)$ for parameter b over a dynamic range, determining a linearized response $\mu(A) \times a + \mu(B) \times b$, where $\mu(A)$ and $\mu(B)$ are linearization constants, spectrally correcting for both $P(a,b,i)$ and $P(0,b,i)$ using a water-based spectral correction to produce $P_W(a,b,i)$ and $P_W(0,b,i)$, and mapping data pairs $(P_W(a,b,i), P_W(0,b,i))$ to $\mu(A) \times a + \mu(B) \times b$ to obtain a beam hardening calibration function.

In still other aspects, the present invention provides a computed tomographic (CT) imaging apparatus having a radiation source and a detector array. The CT imaging apparatus is configured to segment materials in a first pass image generated with a water beam hardening correction to determine projection values contributed by materials other than water or soft tissue, and forward project segmented images for individual materials to obtain projection values for the materials.

In yet other aspects, the present invention provides a computed tomographic (CT) imaging apparatus including a correction for beam hardening in CT images. The apparatus is configured to determine projection data $P(a,b,i)$ for parameters a and b over a dynamic range, where a is a thickness of a first material A, b is a thickness of a second, different material B, i is a detector index, and $P(a,b,i)$ is a logarithmic function of a ratio of an expected signal through a thickness of first material A, b thickness of second, different material B at detector index i and an expected air measurement signal at detector index i. The apparatus is further configured to determine projection data $P(0,b,i)$ for parameter b over a dynamic range, determine a linearized response $\mu(A) \times a + \mu(B) \times b$, where $\mu(A)$ and $\mu(B)$ are linearization constants, spectrally correct for both $P(a,b,i)$ and $P(0,b,i)$ using a water-based spectral correction to produce $P_W(a,b,i)$ and $P_W(0,b,i)$, and map data pairs $(P_W(a,b,i), P_W(0,b,i))$ to $\mu(A) \times a + \mu(B) \times b$ to obtain a calibration function.

It will be appreciated that various configurations of the present invention provide spectral calibration for more than one material without performing extra measurements other than two or more air scans.

DETAILED DESCRIPTION OF THE INVENTION

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighting factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
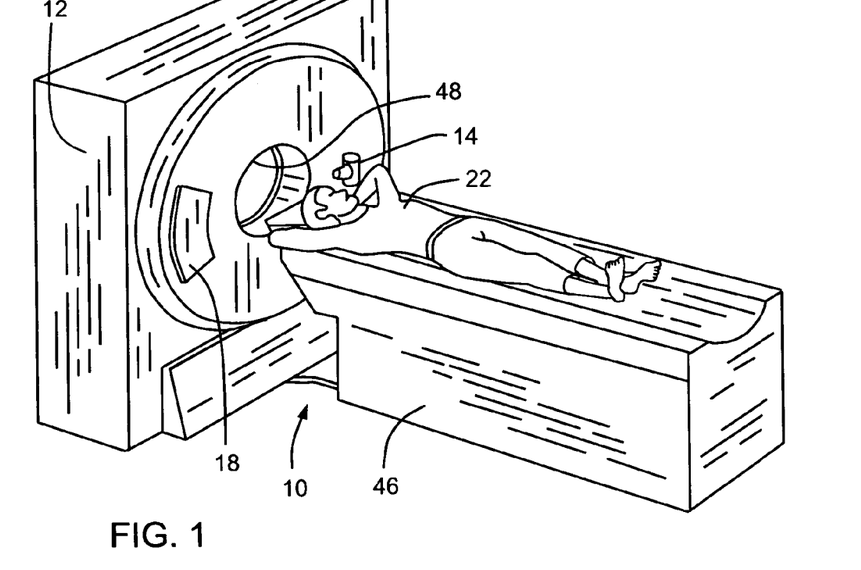
FIG. 1 is a pictorial drawing representative of some configurations of CT imaging apparatus of the present invention.
Figure 2:
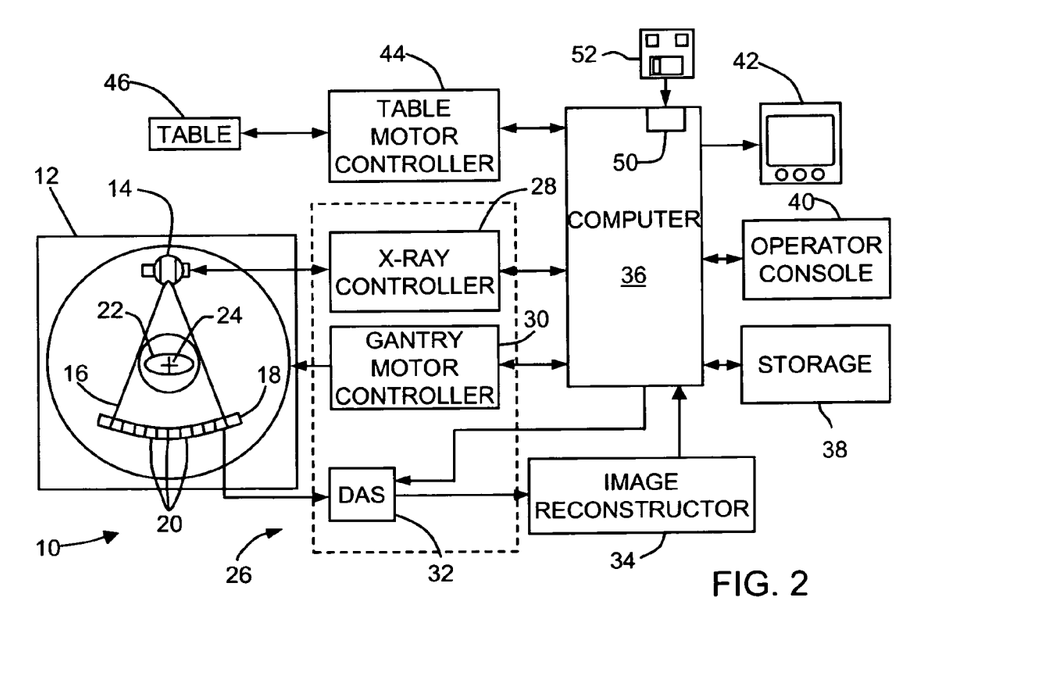
FIG. 2 is a functional block diagram representative of the CT imaging apparatus of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated display 42, for example, a cathode ray tube or other suitable display device, allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a instruction reading or receiving device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

In some configurations of the present invention, a method for correcting artifacts in images produced by CT imaging system 10 is provided. The corrected artifacts are those resulting from the presence of bones, contrast agents, metal implements, and other high-density objects. In some configurations of the present invention, calibration for multiple materials is performed without performing extra physical measurements. A technical effect of such calibration is to generate accurate correction vectors that are useful for removing beam hardening and detector spectral related artifacts in CT images in cases in which an imaged object (which may be a patient, but can be another animate or inanimate object) contains more than one material. Configurations of the present invention are described herein in connection with a two-material object, as these configurations are sufficient to provide an understanding of the generalizations by which other configurations are able to provide corrections for objects having any number of distinct materials.

Figure 3:
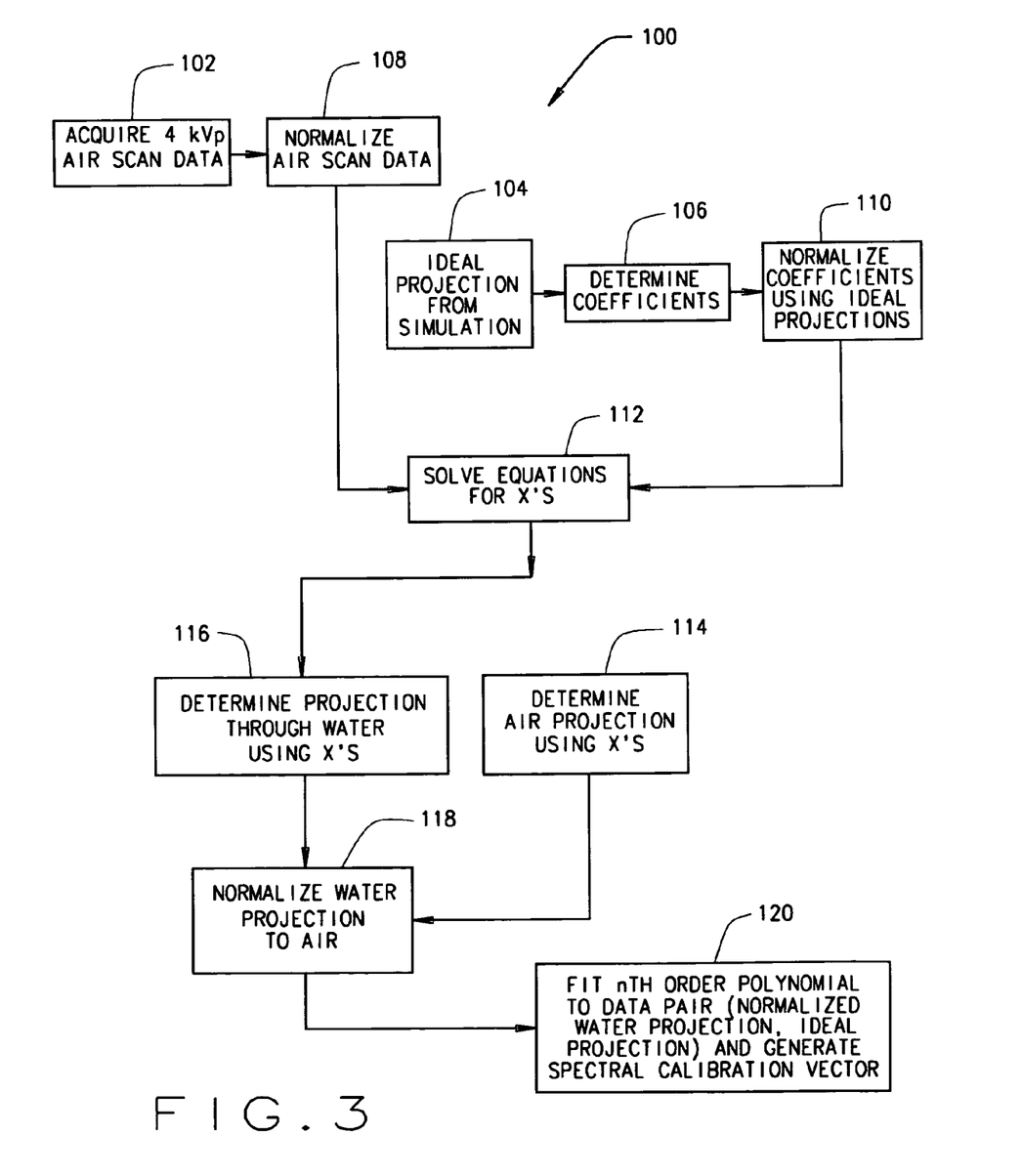
FIG. 3 is a flow chart representative of various configurations of calibration procedures for CT imaging with detector spectral error correction.

FIG. 3 is a flowchart 100 illustrating example processes utilized by CT imaging system 10. Many of the steps shown in flowchart 100 can be performed automatically under control of computer 36 under suitable program control (e.g., a firmware program built into computer 36 or provided device 50). However, it is not required that the steps be performed in an automatic progression. The technical effect of methods and apparatus utilizing processes represented by flowchart 100 is achieved by a user first operating CT imaging system to acquire (i.e., measure) a detected signal dataset $\{D(i,kv)\}$ at 102, where i is the detector element 20 index, for each kVp setting provided by the CT system, and without any object in the path of x-ray beam 16 except for system beam filter 19, if present. In some configurations, there are four kVp settings, so four scans are recorded at 102. In other configurations, a greater or lesser number of scans are recorded. Separately, at 104, ideal projections are simulated. More particularly, in some configurations, the following parameters are defined in the simulation:

$S(E,kv)$ is a spectrum as a function of x-ray kv (kilovolts) and photon energy E;

$b(e,i)$ is a combined material attenuation of the beam filters for detector i (this function can change with time for a dynamically varying beam filter, and in such cases, is also a function of t);

$\mu(A,E)$ is a linear attenuation coefficients of a material A;

$X_n(i)$ are a set of unknown coefficients to be solved;

$T_L$ is the scintillator thickness of the detector elements.

An ideal projection value $P_{ideal}(i,kv)$ is written:

$$P_{ideal}(i,kv) = \Sigma_E \{S(E,kv) \times E \times [1-\exp(-\mu(\text{scintillator},E) \times T_L)] \times \exp(-b(E,i))\} \quad (1)$$

The predicted (i.e., estimated) projection values form a dataset $\{P(i,kv)\}$ that takes into account physical properties of detection components of imaging system 10. The dataset of ideal projection coefficients is determined at 106 from the simulation at 104. (The "detection components of imaging system 10" include detector elements 20, radiation source 14, and filter 19, if present, and other spectral effects introduced by detector array 18.) The predicted projection values are written:

$$P(i,kv) = \Sigma_E \{S(E,kv) \times E \times [1-\exp(-\mu(\text{scintillator},E) \times T_L)] \times \exp(-b(E,i)) \times f(E,i)\} \quad (2)$$

where $f(E,i)$ is the system detection function for photons with energy E. The system detection function $f(E,i)$ can be modeled as a smooth function of E, for example and not by way of limitation, a polynomial with system detection coefficients $X_n(i)$ such as $f(E,i) = X_0(i) + X_1(i) \times E + X_2(i) \times E^2 + X_3(i) \times E^3$.

The acquired dataset $\{D(i,kv)\}$ (subtracting an electronic offset reading) is normalized at 108, using an expression written $D_{norm}(i,kv) = D(i,kv)/\Sigma_i D(i,kv)$, represents the normalized measured data.

The ideal projection data coefficients are normalized at 110, using an expression written $P_{norm}(i,kv) = P(i,kv)/\Sigma_i P_{ideal}(i,kv)$.

In various configurations of the present invention, the various values of system detection coefficients $X_n(i)$ are determined at 112 for each detector element using a relationship written $P_{norm}(i,kv) = D_{norm}(i,kv)$ by solving a set of linear equations, if system detection function $f(E,i)$ is expressed in a polynomial form as shown herein. Otherwise, if necessary, nonlinear or numerically-derived techniques can be used to determine the system detection function $f(E,i)$.

In some configurations, an air projection dataset $\{A(i,kv)\}$ is estimated at 114 using the values of $X_n(i)$. The model $A(i,kv)$ is written:

$$A(i,kv) = \Sigma_E \{S(E,kv) \times E \times [1-\exp(-\mu(\text{scintillator},E) \times T_L)] \times \exp(-b(E,i)) \times f(E,i)\}.$$

Also, at 116, a projection dataset through water $\{W(i,kv,L)\}$ for path length L is estimated at 116 using the values of $X_n(i)$:

$$W(i,kv,L) = \Sigma_E \{S(E,kv) \times E \times [1-\exp(-\mu(\text{scintillator},E) \times T_L)] \times \exp(-b(E,i)) \times f(E,i) \times \exp(-\mu(\text{water},E) \times L)\}.$$

Next, the water projection is logarithmically normalized to the air projection at 118 to produce a projection value Proj(i,kv,L) written:

$$\text{Proj}(i,kv,L) = -\log[W(i,kv,L)/A(i,kv)].$$

An nth order polynomial is fitted to the data pair (normalized water projection, ideal projection)=(Proj(i,kv,L),Ideal(i,kv,L)) to generate the spectral calibration vector at 120. The normalized water projection data Proj(i,kv,L) is mapped to the ideal projection value, which is written as:

$$\text{Ideal}(i,kv,L) = \mu \times L,$$

where μ is a constant that is equal to the water linear attenuation at the average x-ray energy for a given kVp, and spectral cal vectors are also generated. The purpose of spectral cal for water is to linearize a measured projection value to water path length. More particularly, a mapping function Proj(i,kv,L)→Ideal(i,kv,L) is the spectral calibration, which can either be in the form of a look-up table or in some functional form. A polynomial fit can characterize the mapping. The coefficients of the mapping polynomial can be obtained by fitting data pairs (Proj(i,kv,L),Ideal(i,kv,L)) generated at various water path length L.

Steps 114, 116, 118, and 120 can be iterated with different bowtie filter 19 shapes, if bowtie filter 19 (or another adjustable filter) is present to obtain different mappings for different values of b(E,i). The different mappings are especially useful for applying a spectral correction to adaptive or dynamic beam filters that change the beam filter shape before or during patient scanning.

Thus, an ideal spectral effect is modeled by simulation of an x-ray beam spectrum and its interaction with materials such as filters in the beam path and water phantoms. Deviation from the ideal model is determined from the measurements at multiple kVp's. Detector detection efficiency as a function of photon energy and any additional filtration in the beam path is modeled as a polynomial function directly as shown herein, or two distinct materials plus a polynomial, or any other smooth functional form. System detection coefficients $X_n(i)$ are determined from measurements of air scans through known beam filters or through air scans without beam filters, at a plurality of kVp's. The number of kVp's required in some configurations is equal to or greater than the number of unknown coefficients in the functional form, or, in some other configurations, a least squares method of obtaining coefficients is used. The functional form can be further reduced to linear terms of the unknown coefficients, simplifying the process of obtaining the solutions of the unknown coefficients. Upon obtaining the coefficients in the functional form, the detected signal of each detector element through the beam filter and through a given thickness of water is determined for a spectrum at a given kVp. The spectral errors of any detector element can be determined by comparing the calculated signal, normalized to a calculated air signal, with the negative of the logarithm taken and incorporating the detection functional form, to the ideal signal (or a corrected signal). The ideal signal used here is a linear function of the water penetration length. By making such determinations for all penetration lengths of water relevant to imaging (for example, in a medical imaging application), a data pair set of predicated signal and ideal signal is built for each detector element. This data pair set provides a direct spectral correction for removing beam hardening in water and eliminating detector errors. This data pair set can be fitted by a polynomial, providing fast spectral correction. Moreover, the spectral correction can be performed dynamically or statically for any beam filter shape, upon the determination of the system detection coefficients $X_n(i)$. For example and without limitation, a spectral correction can be applied to adaptive beam filters that change the beam filter shape before or during patient scanning for radiation dose reduction.

Figure 4:
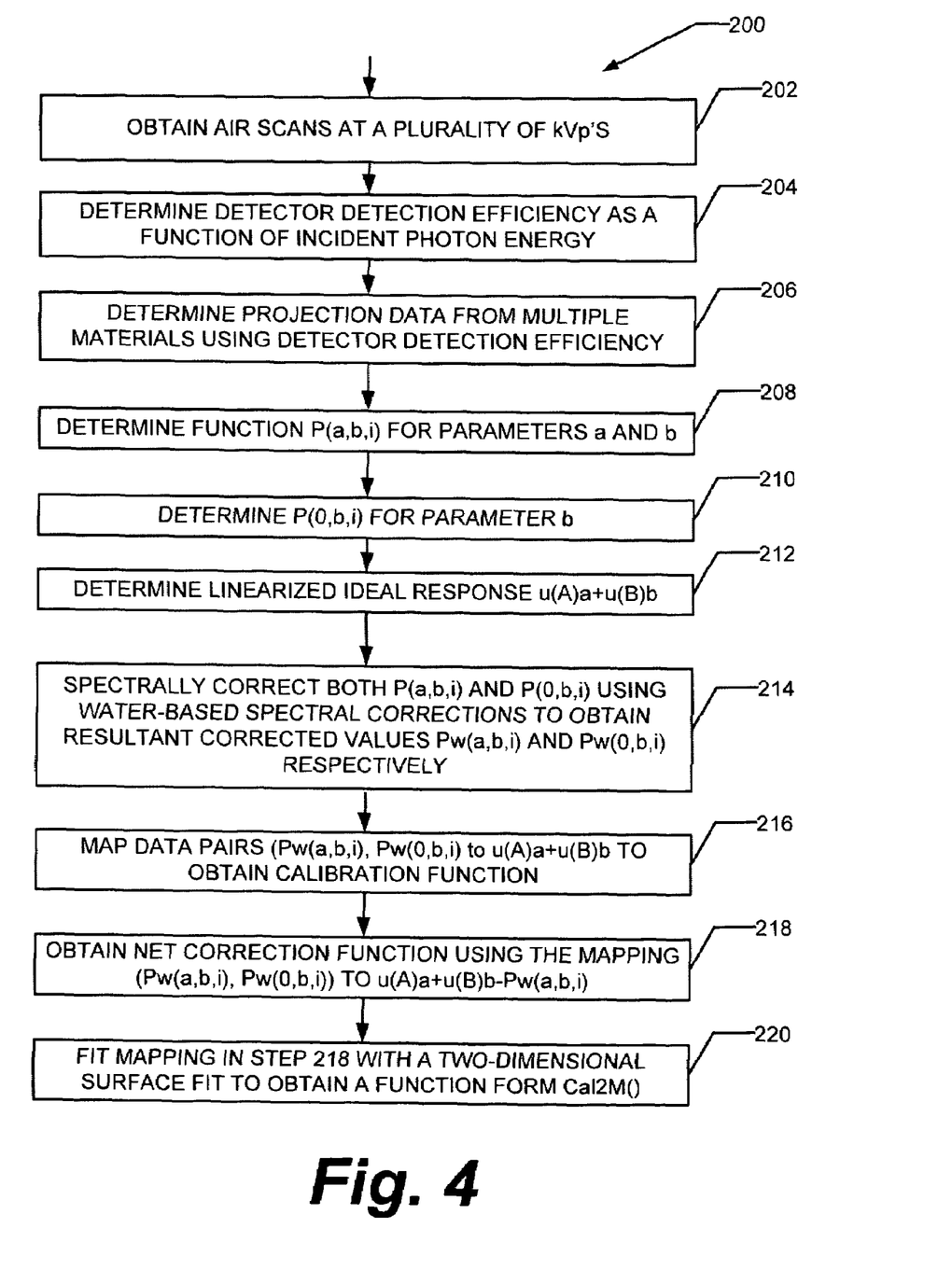
FIG. 4 is a flow chart representative of various configurations of the present invention that provide correction of CT image artifacts produced by high density materials.

In some configurations of the present invention and referring to flow chart 200 of FIG. 4, a technical effect of the present invention is achieved by first, at 202, obtaining air scans at a plurality of kVp's. In some configurations, detector detection efficiency is obtained at 204 as a function of the incident photon energy E. This efficiency is denoted as ƒ(E,i), where i is the detector channel index. (A "detector channel" corresponds to a single detector element 20 or a group of detector elements 20, depending upon whether the signals from detector elements 20 are processed individually or are combined in groups and processed as though the group of elements constituted a single, larger element.) Projection data from multiple materials are determined at 206 using the detector detection efficiency, which itself is determined utilizing a detector detection efficiency function ƒ(E,i) at 206.

At this point, it is useful to introduce as variables:
S(E,i), the incident X-ray spectrum for a given detector channel i, already incorporated detector stopping power;
μ(A,E), the linear attenuation coefficients of material A;
Air(i), the expected air measurement signal;
M(a,b,i), the expected signal through a thickness of first material A, and b thickness of second, different material B; and
P(a,b,i), the projection value through a thickness a of material A, and a thickness b of material B.

If the input X-ray spectrum S(E,i) is accurately modeled or measured, the measurement of detection efficiency ƒ(e,i) can be determined using the modeled or measured x-ray spectrum and material linear attenuation coefficients, thereby allowing the characteristic and performance of the CT system to be determined through simulation. For a detection system that records the integrated photon energy, such as a scintillator-PIN diode combination detector, the following can modeled accurately:

$$\text{Air}(i) = \Sigma_E \{S(E,i) \times E \times [1-\exp(-\mu(\text{scintillator},E) \times T_L)] \times \exp(-b(E,i)) \times ƒ(E,i)\} \quad (3)$$

Through a two-material object, the expected signal through a thickness of material A, and b thickness of material B is written:

$$M(a,b,i) = \Sigma_E \{S(E,i) \times E \times [1-\exp(-\mu(\text{scintillator},E) \times T_L)] \times \exp(-b(E,i)) \times \exp(-\mu(A,E) \times a - \mu(B,E) \times b) * ƒ(E,i)\} \quad (4)$$

The measured projection data through a thickness a of material A, and a thickness b of material B is written:

$$P(a,b,i) = -\log[M(a,b,i)/\text{Air}(i)]. \quad (5)$$

To calibrate a one-material system, some configurations of the present invention provide a mapping function or table F( ) that provides a mapping written:

$$F(P(a,0,i)) = \mu(A) \times a \quad (6)$$

where μ(A) is a linearization constant. Details for how to obtain function F( ) for attenuation through a single material are described in FIG. 3 and the description thereof.

To fully identify a two-material system, two projection values are needed, for example, P(a,b,i) with the contribution from all the materials, and P(0,b,i) for one selected material. More generally, to fully identify an N-material system, N projection values are needed. Thus, calibrations for at least two different materials are used to determine at least one of a multiple-material calibration function or a multiple-material calibration look-up table. Both of these forms (i.e., the function and the table) have a number of input parameters equal to the number of materials. In either form, the multiple-material calibration is useful for providing accurate beam hardening related image artifact corrections.

To simplify the description, a two-material system will be identified as an example. Without loss of generality, material A in the example herein is water, and material B is bone, although materials A and B are not restricted to these materials. For example, although material A would often be identified as water in medical configurations, B may often be iodine or a surgically-implanted material rather than bone. A and B may also represent other, different materials, particularly in non-medical configurations. It will be appreciated, however, that more than two materials may comprise the system, and that the materials may be different from water and/or bone. For example, the materials may include foreign objects such as a knife, a bullet, "bb"s, shotgun pellets, arrow heads, etc. Also, calibration is not limited to 2 materials. For example, and not by way of limitation, a three material system may include calibration for water, bone, and iodine.

In building a two-material system calibration, parameters a and b are input, and P(a,b,i) and P(0,b,i) are output. A technical effect of the present invention is to capture a relationship between data pair (a,b) and (P(a,b,i), P(0,b,i)) and utilize this mapping to store a transfer function in a memory for calibration of an imaging system.

In the correction phase, projection value P(0,b,i) attributable to bone is not known directly from measurements. However, it is well known that this projection value can be obtained from a first-passed image corrected only with a general water-based spectral correction. By clipping the first-passed image to obtain a bone-only image and by forwarding-projecting the bone-only image, the bone projection value P(0,b,i) can be determined.

Spectral correction for a two (or more) material system utilizing a detector detection efficiency function is similar to that of a one-material system in equation (6), except that the second material response is linearized in various configurations of the present invention. The calibration for the different materials thus becomes "multiple material calibration data." For example, $$F(P(a,b,i)) = \mu(A) \times a + \mu(B) \times b \quad (7)$$

To identify the two path lengths a and b for the two materials, two input parameters are needed for the calibration function. In some configurations, the total projection values as well as the individual projection values from one or the other of the two materials, such as bone, are used. In other configurations, other sets of N parameters are used. The sets of parameters are selected to allow one to solve for the N path lengths of N materials.

In some configurations of the present invention, segmentation of materials in a first-pass image is generated with a water beam hardening correction to determine projection values contributed by materials other than water or soft tissue, and a segmented image for individual materials is forward projected to obtain projection values from each of the individual materials. In some of these configurations, total projection values and individual projection values are used as inputs to the multiple-material calibration function to produce a correction value for spectral related image artifact removal.

In a two material configuration in which the total projection and the projection from one or the other of the two materials are used, equation (7) is expressed as:

$$F(P(a,b,i), P(0,b,i)) = \mu(A) \times a + \mu(B) \times b) \quad (8)$$

The multiple material calibration function F( ) in equation (8) can be obtained by experimentally calibrating the scanner with a phantom comprising a combination of materials made of water and bone of various thickness. Some configurations of the present invention generate a multiple material calibration function for at least one combination of materials, e.g., water and bone, water and iodine, or water and a surgically-implanted material. In instances in which this type of measurement is difficult to perform, the calibration function can be computed through software simulation using the already captured detector performance $f(E,i)$.

Thus, in some configurations of the present invention, at 208, the function P(a,b,i) is determined for parameters a and b, preferably over the entire dynamic range using equation (5). Next, at 210, P(0,b,i) is determined for parameter b, preferably over its entire dynamic range, using equation (5). At 212, the linearized ideal response $\mu(A) \times a + \mu(B) \times b$ is determined. In some configurations of the present invention, the linearization constant for each of the different materials is adjusted to reduce a difference between corrected and uncorrected data. This difference can be used to reconstruct a correction image and this correction image can be added to an original image. In some configurations, the difference is added to a projection corrected for water spectral hardening to reconstruct a further corrected image.

Next, at 214, both P(a,b,i) and P(0,b,i) values are spectrally corrected using water-based spectral corrections to obtain resultant corrected values are $P_W(a,b,i)$ and $P_W(0,b,i)$, respectively. Parameter P( ) is changed to $P_W( )$ in some configurations, such as the one presently being described, because the spectral correction of additional material in this configuration is based on projection data that are first corrected by a single material spectral correction, e.g., a water-based spectral correction.

At 216, data pairs $(P_W(a,b,i), P_W(0,b,i))$ are mapped to $\mu(A) \times a + \mu(B) \times b$ to obtain the calibration function. At 218, a net correction function is obtained using the mapping $(P_W(a,b,i), P_W(0,b,i))$ to $\mu(A) \times a + \mu(B) \times b - P_W(a,b,i)$. More specifically, the net correction is determined as the difference between two-material spectrally corrected data and one-material spectrally corrected data (referred to as original data).

At 220, some configurations of the present invention fit the mapping produced at 218 with a 2D surface fit to yield a functional form for faster correction. This functional form Cal2M() of the mapping is written:

$$\text{Cal2M}(P_W(a,b,i), P_W(0,b,i)) = \mu(A) \times a + \mu(B) \times b - P_W(a,b,i) \quad (9)$$

The function Cal2M( ) provides an additional correction due to the second material b in the beam path. Input parameter $P_W(a,b,i)$ is the measured data. However, in practice, $P_W(0,b,i)$ can be obtained from forward-projecting the image containing material b only. Calibration function Cal2M( ) provides an accurate and robust way of removing beam-hardening artifacts in CT images due to high-density material, in cases in which the composition of the high-density material is known and this second material can be identified in the image. For example, in some configurations of the present invention, an object is scanned using CT imaging system 10 to obtain projection data of the object, and a calibration for different materials is used to remove artifacts arising from variations in detector spectral response for x-rays hardened by the different materials. Calibration function Cal2M( ) is generated for each individual detector channel, therefore, the correction removes artifacts due to variation in detector spectral response when more than one material is present in the scanned object as well as removing a general beam hardening artifact.

Many of the steps shown in flowcharts 100 and 200 and/or discussed in this description can be performed automatically under control of computer 36 under suitable program control.

For example, a firmware program can be built into computer 36 or provided in a suitable form to device 50, such as computer instructions on CD-ROM or on other media. However, it is not required that the steps be performed in an automatic progression.

It will thus be appreciated that configurations of the present invention utilizes detector characteristics to provide accurate and robust correction of image artifacts arising from beam hardening in material other than water or soft tissue without requiring time-consuming measurements. The detector characteristics are used to compute calibration vectors for systems comprising two or more materials. Configurations of the present invention accurately correct for beam hardening in high-density materials and do not require empirical algorithms that often need parameter adjustment, as is often used in prior art methods for making head images. Moreover, configurations of the present invention provide corrections that remove detection spectral variation among detector channels in images containing high-density material.

While the invention has been described in terms of various specific embodiments, those skilled in the art will recognize that the invention can be practiced with modification within the spirit and scope of the claims.

What is claimed is:

1. A method for determining a correction for beam hardening in CT images in a CT imaging apparatus, said method comprising:
    obtaining air scans at a plurality of kVp's;
    determining detection efficiencies for detector elements of the CT imaging apparatus;
    estimating a first set of projection values through a combination of at least two different materials of different thicknesses based on at least a combined material attenuation of the beam filters positioned between a radiation source and the detector elements, said different materials are objects other than the beam filters;
    estimating a second set of projection values through one of the two different materials based on the combined material attenuation of the beam filters;
    spectrally calibrating said materials utilizing a detector detection efficiency function, said spectral calibration for said different materials thereby becoming multiple material calibration data;
    determining a transfer function that translates the first set of estimated projection values and the second set of estimated projection values into ideal projection values for at least two of said different materials; and
    storing the transfer function as the beam hardening calibration function for images of the CT imaging apparatus.

2. A method in accordance with claim 1 further comprising determining said detection efficiency function utilizing a modeled or measured x-ray spectrum and material linear attenuation coefficients.

3. A method in accordance with claim 1 further comprising scanning an object with the CT imaging system to obtain projection data of the object, and using said transfer function to remove artifacts arising from variation in detector spectral response for x-rays hardened by said different materials.

4. A method in accordance with claim 1 further comprising using the multiple material calibration data to determine at least one member of the group consisting of a multiple-material calibration function and a multiple-material calibration look-up table, wherein a number of input parameters is equal to the number of materials.

5. A method in accordance with claim 4 wherein said determined member of said group is a multiple-material calibration function, and further comprising utilizing the multiple-material calibration function to determine a net correction function after correcting initial projection data using a spectral correction for a single material.

6. A method in accordance with claim 5 wherein the multiple-material calibration function is generated for at least one combination of materials selected from the group of combinations consisting of {water, bone}, {water, iodine}, and {water, surgically-implanted material}.

7. A method in accordance with claim 5 wherein the single material is water.

8. A method in accordance with claim 7 further comprising using segmentation of materials in a first-pass image generated with a water beam hardening correction to determine projection values contributed by materials other than water or soft tissue, and forward projecting a segmented image for individual materials to obtain projection values from each said individual material.

9. A method in accordance with claim 8 further comprising utilizing total projection values and individual projection values as inputs to the multiple-material calibration function to produce a correction value for spectral related image artifact removal.

10. A method in accordance with claim 1 wherein the transfer function is a product of a linearization constant unique to at least two different said materials and a path length of said at least two different said materials.

11. A method in accordance with claim 10 further comprising adjusting the linearization constant to reduce a difference between corrected data and uncorrected data.

12. A method in accordance with claim 11 further comprising using the difference between the corrected data and the uncorrected data to reconstruct a correction image and adding the correction image to an original image.

13. A method in accordance with claim 11 further comprising adding the difference between the corrected data and the uncorrected data to a projection corrected for water spectral hardening to reconstruct a further corrected image.

14. A method for determining a correction for beam hardening in computed tomographic (CT) images, said method comprising:
    determining a detector detection efficiency $f(E,i)$, where $f(E,i)$ is a function of at least a material linear attenuation coefficient $\mu(A,E)$, A is a first material, E is incident photon energy, and i is a detector index;
    determining projection data $P(a,b,i)$ for parameters a and b over a dynamic range, where a is a thickness of the first material A, b, is a thickness of a second, different material B, and $P(a,b,i)$ is a logarithmic function of a ratio of an expected signal through a thickness of first material A, b, thickness of second, different material B at detector index i and an expected air measurement signal at detector index i, wherein determining projection data $P(a,b,i)$ is based on at least a combined material attenuation $b(e,i)$ of beam filters positioned between a radiation source and a detector element, the first and second materials are objects other than the beam filters;
    determining projection data $P(0,b,i)$ for parameter b over a dynamic range;
    determining a linearized response $\mu(A) \times a + \mu(B) \times b$, where $\mu(A)$ and $\mu(B)$ are linearization constants;
    spectrally correcting for both $P(a,b,i)$ and $P(0,b,i)$ using a water-based spectral correction to produce $P_w(a,b,i)$ and $P_w(0,b,i)$; and
    mapping data pairs $(P_w(a,b,i), P_w(0,b,i))$ to $\mu(A) \times a + \mu(B) \times b$ to obtain a beam hardening calibration function.

15. A method in accordance with claim 14 further comprising mapping from $P_w(a,b,i),P_w(0,b,i))$ to $\mu(A) \times a + \mu(B) \times b - P_w(a,b,i)$ to obtain a difference between two-material spectrally corrected data and one-material spectrally corrected data.

16. A method in accordance with claim 15 further comprising fitting the difference between two-material spectrally corrected data and one-material spectrally corrected data with a two dimensional surface fit to obtain a functional form Cal2M( ).

17. A method in accordance with claim 14 wherein material A is water and material B is bone.

18. A computed tomographic (CT) imaging apparatus comprising a radiation source and a detector array said CT imaging apparatus configured to:
- segment materials in a first pass image generated with a water beam hardening correction to determine projection values contributed by materials other than water or soft tissue, wherein the water beam hardening correction is based on at least an expected air measurement signal acquired via an air scan with an X-ray beam path clear of any objects other than beam filters; and
- forward project segmented images for individual materials to obtain a first set of projection values for said materials based on at least a combined material attenuation of the beam filters positioned between the radiation source and the detector array, the individual materials are objects other than the beam filters;
- forward project segmented images for one of said individual materials to obtain a second set of projection values for said material based on the combined material attenuation of the beam filters;
- spectrally correct for both said first set of projection values and said second set of projection values to produce data pairs used in a beam hardening calibration function.

19. A computed tomographic (CT) imaging apparatus including a correction for beam hardening in CT images, said apparatus configured to:
- determine projection data $P(a,b,i)$ for parameters a and b over a dynamic range, where a is a thickness of a first material A, b is a thickness of a second, different material B, i is a detector index, and $P(a,b,i)$ is a logarithmic function of a ratio of an expected signal through a thickness of first material A, b thickness of second, different material B at detector index i and an expected air measurement signal at detector index i, wherein determining projection data $P(a,b,i)$ is based on at least a combined material attenuation $b(e,i)$ of beam filters positioned between a radiation source and a detector element, the first and second materials are objects other than the beam filters and wherein the expected air measurement signal at detector index i is based on an air scan obtained with an X-ray beam path clear of any materials other than the beam filters;
- determine projection data $P(0,b,i)$ for parameter b over a dynamic range;
- determine a linearized response $\mu(A) \times a + \mu(B) \times b$, where $\mu(A)$ and $\mu(B)$ are linearization constants;
- spectrally correct for both $P(a,b,i)$ and $P(0,b,i)$ using a water-based spectral correction to produce $P_w(a,b,i)$ and $P_w(0,b,i)$; and
- map data pairs $(P_w(a,b,i),P_w(0,b,i))$ to $\mu(A) \times a + \mu(B) \times b$ to obtain a calibration function.

20. An apparatus method in accordance with claim 19 further configured to map from $(P_w(a,b,i),P_w(0,b,i))$ to $\mu(A) \times a + \mu(B) \times b - P_w(a,b,i)$ to obtain a difference between two-material spectrally corrected data and one-material spectrally corrected data.

21. An apparatus in accordance with claim 20 further configured to fit the difference between two-material spectrally corrected data and one-material spectrally corrected data with a two dimensional surface fit to obtain a functional form Cal2M( ).

22. An apparatus in accordance with claim 19 wherein material A is water and material B is bone.

23. A computed tomographic (CT) imaging apparatus including a correction for beam hardening in CT images, said apparatus configured to:
- determine projection data for a plurality of parameters over a dynamic range and over detector indices, wherein parameters relate to a plurality of materials and thicknesses of said materials; and the projection data is a logarithmic function of a ratio of, on the one hand, an expected signal for a given said material and a given thickness of said given material, and, on the other hand, an expected air measurement signal at a given detector index, said projection data thereby being combined material projection data, wherein determining projection data is based on at least a combined material attenuation of beam filters positioned between a radiation source and detector elements, the materials are objects other than the beam filters and wherein the expected air measurement signal at the given detector index is based on an air scan obtained with an X-ray beam path clear of any objects other than the beam filters;
- determine separate material projection data over a dynamic range for each said material separately;
- determine a linearized response including linearization constants for each said material;
- spectrally correct said combined material projection data to produce spectrally corrected combined material projection data;
- map sets of said spectrally corrected combined material projection data and said separate material projection data to said linearized response to obtain a calibration function.

* * * * *